United States Patent [19]

Choi et al.

[11] Patent Number: 5,756,817
[45] Date of Patent: May 26, 1998

[54] O-CARBAMOYL-PHENYLALANINOL COMPOUNDS, THEIR PHARMACEUTICALLY USEFUL SALTS AND PROCESS FOR PREPARING THE SAME

[75] Inventors: Yong Moon Choi, Towaco, N.J.; Dong Il Han, Taejon, Rep. of Korea; Yong Kil Kim, Taejon, Rep. of Korea; Hun Woo Shin, Taejon, Rep. of Korea; Jeong-Han Park, Flanders, N.J.

[73] Assignee: Yukong Limited, Seoul, Rep. of Korea

[21] Appl. No.: 726,675

[22] Filed: Oct. 7, 1996

Related U.S. Application Data

[63] Continuation-in-part of Ser. No. 596,496, Feb. 5, 1996, Pat. No. 5,705,640.

[30] Foreign Application Priority Data

Feb. 11, 1995 [KR] Rep. of Korea ............... 1995-2543

[51] Int. Cl.$^6$ ............................................... C07C 261/00
[52] U.S. Cl. ...................... 560/115; 544/172; 544/389; 546/226; 548/531; 560/32; 560/163; 560/164
[58] Field of Search .............................. 560/163, 115, 560/164, 32; 548/531; 546/226; 544/169, 389

Primary Examiner—Michael L. Shippen
Attorney, Agent, or Firm—Abelman, Frayne & Schwab

[57] ABSTRACT

The present invention relates to a racemic or enantiomerically enriched O-carbamoyl-phenylalaninol compound represented by the following structural formula V and pharmaceutically acceptable salts thereof to treat diseases of the central nervous system:

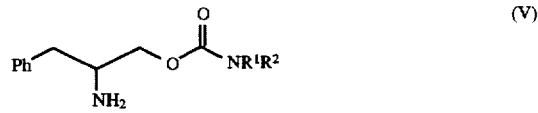

wherein Ph is a phenyl group as described as follows:

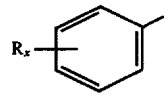

wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms, and x is an integer from 1 to 3, with the proviso that R is the same or different when x is 2 or 3, $R^1$ and $R^2$ may be the same or different from each other and are independently selected from the group consisting of hydrogen, lower alkyl of 1 to 8 carbon atoms, aryl, arylalkyl, cyclic propyl and 5 to 7-membered aliphatic cyclic compounds, and $R^1$ and $R^2$ may be joined to form a 5 to 7-membered cyclic compound which may comprise zero to one additional nitrogen atom substituted with a member selected from the group consisting of hydrogen, alkyl, and aryl groups, or zero to one oxygen atom directly unconnected, excluding the instance where R, $R^1$, and $R^2$ are all hydrogen, and the pharmaceutically acceptable salts thereof.

The present invention also relates to O-carbamoyl-(D)-phenylalaninol compounds, represented by the following structural formula IX:

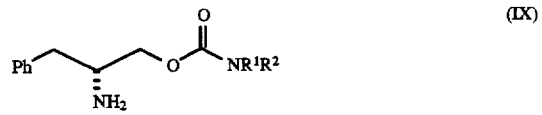

wherein Ph, $R^1$, and $R^2$ are as described above, and the pharmaceutically acceptable salts thereof.

35 Claims, No Drawings

5,756,817

O-CARBAMOYL-PHENYLALANINOL COMPOUNDS, THEIR PHARMACEUTICALLY USEFUL SALTS AND PROCESS FOR PREPARING THE SAME

CROSS REFERENCE TO RELATED APPLICATION

The present application is a continuation-in-part of U.S. application Ser. No. 08/596,496, filed Feb. 5, 1996, now U.S. Pat. No. 5,705,640.

BACKGROUND OF THE INVENTION

1. Field of the Invention

The present invention relates, in general, to novel phenylalkylamino carbamate compounds and pharmaceutically useful salts thereof for treating diseases of the central nervous system. More particularly, the present invention relates to racemic mixtures or enantiomerically enriched O-carbamoylphenylalaninol compounds and pharmaceutically useful salts thereof 2. Description of the Prior Art Phenylethylamine derivatives, one important class of therapeutical medicines useful for managing central nervous system (CNS) diseases, have been used mainly to treat obesity, narcolepsy, minimal brain dysfunction and mild depression.

Organic carbamates have been effectively used for controlling various CNS disorders. For example, the J. Am. Chem. Soc., 73, 5779 (1951) discloses 2-methyl-2-propyl-1,3-propandiol dicarbamate and its pharmaceutical activity was verified in J. Pharmacol. Exp. Ther., 104, 229 (1952).

In addition, there are many carbamate compounds that are suggested as therapeutics for CNS diseases in the prior art. For example, U.S. Pat. Nos. 2,884,444 and 2,937,119 disclose carbamates, such as 2-phenyl-1,3-propandiol dicarbamate and isopropylmeprobamate, respectively. These compounds are found to be very effectively used as therapeutics for treating CNS disorders, especially as antiepileptics and centrally acting muscle relaxants. Research in the development of carbamate therapeutics for CNS diseases has been and continues to be actively pursued.

The recent design of pharmacologically useful compounds has been based on amino acids or the derivatives thereof, which is mainly attributable to the fact that many of the compounds found in biological systems come from amino acids or the derivatives thereof. In addition, in most cases, the function of a pharmaceutically useful compound is effected after it binds to an enzyme or receptor, which may trigger the regulatory mechanisms of the enzyme or receptor.

SUMMARY OF THE INVENTION

As a result of intensive and thorough research, the present inventors found that O-carbamoyl-phenylalaninol compounds are pharmaceutically useful for CNS disorders, especially for depression and anxiety.

Accordingly, it is a principal object of the present invention to provide racemic or enantiomerically enriched O-carbamoyl-phenylalaninol carbamate compounds, represented by the following structural formula V:

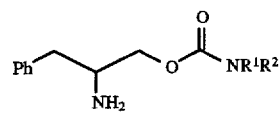

(V)

wherein Ph is a phenyl group as described as follows:

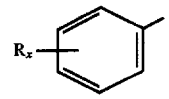

wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms, and x is an integer from 1 to 3, with the proviso that R is the same or different when x is 2 or 3, $R^1$ and $R^2$ may be the same or different from each other and are independently selected from the group consisting of hydrogen, lower alkyl of 1 to 8 carbon atoms, aryl, arylalkyl, cyclic propyl and 5 to 7-membered aliphatic cyclic compounds, and $R^1$ and $R^2$ may be joined to form a 5 to 7-membered cyclic compound which may comprise zero to one additional nitrogen atom substituted with a member selected from the group consisting of hydrogen, alkyl, and aryl groups, or zero to one oxygen atom directly unconnected, excluding the instance where R, $R^1$, and $R^2$ are all hydrogen, and the pharmaceutically acceptable salts thereof.

More specifically, it is a principal object of the present invention to provide O-carbamoyl-(D)-phenylalaninol compounds, represented by the following structural formula IX: (alternatively, "D" can be referred to as R-configuration at chiral center in structural formula IX)

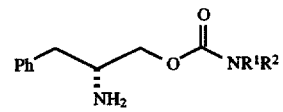

(IX)

wherein Ph is a phenyl group as described as follows:

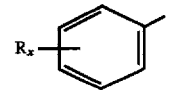

wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms, and x is an integer from 1 to 3, with the proviso that R is the same or different when x is 2 or 3, $R^1$ and $R^2$ may be the same or different from each other and are independently selected from the group consisting of hydrogen, lower alkyl of 1 to 8 carbon atoms, aryl, arylalkyl, cyclic propyl and 5 to 7-membered aliphatic cyclic compounds, and $R^1$ and $R^2$ may be joined to form a 5 to 7-membered cyclic compound which may comprise zero to one additional nitrogen atom substituted with a member selected from the group consisting of hydrogen, alkyl, and aryl groups, or zero to one oxygen atom directly unconnected, excluding the instance where R, $R^1$, and $R^2$ are all hydrogen, and the pharmaceutically acceptable salts thereof.

DETAILED DESCRIPTION OF THE INVENTION

In accordance with the present invention, the racemic or enantiomerically enriched O-carbamoyl-phenylalaninols represented by the structural formula V and pharmaceutically acceptable salts thereof can be prepared by the following steps starting from readily available starting materials represented by the following structural formula II:

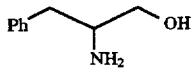
(II)

wherein Ph is the same as defined above.

It should be noted that the stereochemistry of the final products (V and IX) depends solely on that of the starting material (II), for example, a starting material (II) with D-enantiomer yields only a product with D-enantiomer (IX).

The first method for preparing the novel compounds of the general structural formula V will be described in detail below.

O-Carbamoyl-phenylalaninols of structural formula (II) are reacted with benzyl chloroformate in a basic aqueous solution to synthesize N-benzyloxycarbonyl-phenylalaninol, represented by the following structural formula III:

(III)

wherein Cbz is benzyloxycarbonyl group. Then, N-benzyloxycarbonyl-phenylalaninol of structural formula (III) is subjected to carbamoylation with phosgene (or 1,1'-carbonyldiimidazole) in the presence of an amine base, represented by the following general formula (VI):

 (VI)

wherein $R^1$ and $R^2$ are the same as defined above, to produce O-carbamoyl-N-benzyloxycarbonyl-phenylalaninol, represented by the following structural formula (IV):

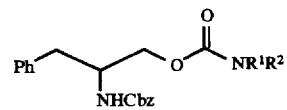
(IV)

wherein $R^1$ and $R^2$ are the same as defined above, deprotecting the benzyloxycarbonyl group from O-carbamoyl-N-benzyloxycarbonyl-phenylalaninol of the structural formula (IV) through hydrogenolysis in the presence of a catalyst, to yield O-carbamoyl-phenylalaninol compound, represented by the structural formula (V) as shown above, wherein $R^1$ and $R^2$ are the same as defined above; and treating O-carbamoyl-(D)-phenylalaninol compound of structural formula (V) with an anhydrous acid, in an ethereal solution without further purification, to give a pharmaceutically acceptable salt thereof, represented by the following structural formula (I):

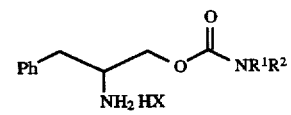
(I)

wherein $R^1$ and $R^2$ are the same as defined above and HX is an acid capable of forming a pharmaceutically useful salt with the intramolecular basic nitrogen atom.

This procedure for preparing the compound of structural formula (I) is summarized in Reaction Scheme I set forth below.

REACTION SCHEME I

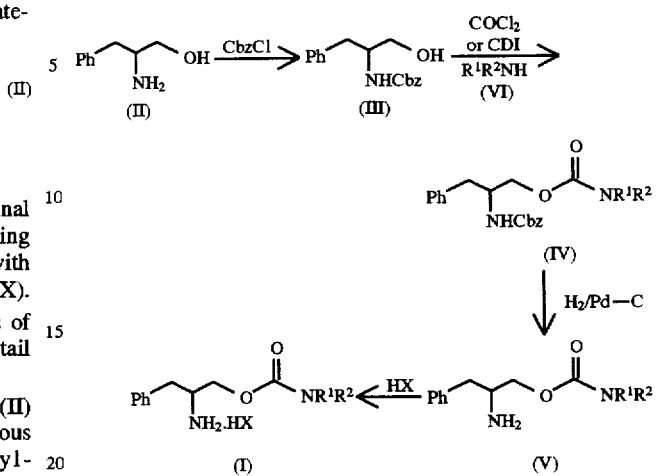

As shown in Reaction Scheme I, phenylalaninol (II) is first reacted with benzyl chloroformate in a basic aqueous solution, to give N-benzyloxycarbonyl-phenylalaninol (III), which is subjected to carbamoylation with phosgene in the presence of an amine base. Ammonolysis of the carbamoylated intermediate is carried out and an amine represented by the general formula VI is used to produce O-carbamoyl-N-benzyloxycarbonyl-phenylalaninol (IV) in a high yield within a short period of time.

Removal of the benzyloxycarbonyl group, a nitrogen protecting group, from the O-carbamoyl-N-benzyloxycarbonyl-phenylalaninol (IV) through hydrogenolysis in the presence of a catalyst, affords O-carbamoyl-phenylalaninol (V) which is, then, treated with an anhydrous acid (HX) in an ether solution without further purification, to provide the salts (I) of O-carbamoyl-phenylalaninol. In Reaction Scheme I, HX represents an acid suitable for the formation of pharmaceutically acceptable salts with the intramolecular basic nitrogen atom.

Details of the reaction conditions described in Reaction Scheme I are as follows. In the first step, the concentration of the starting material (II) is between about 0.1 and 3.0 mole and benzyl chloroformate is used at about 1 to about 2 equivalents. The basic aqueous solution has a pH value between about 7 and about 14 and the conversion reaction is carried out at temperatures ranging from about $-10°$ to about $70°$ C.

For the conversion of the compound (III) to the compound (IV), about 1 to about 2 molar equivalent of phosgene, either neat or as a solution in toluene, is used at about 0.01 to about 2 molar concentration of the compound (III). Halogenated alkanes such as methylene chloride, aromatic solvents, such as toluene, or mixtures thereof, can be used as a solvent. Use of a base such as acid scavenger is recommended. Typically, a tertiary amine, such as triethylamine, diisopropylethylamine, triisopropylamine, DBU (1,6-diazabicyclo[5.4.0]undec-7-ene), DBN (1,5-diazabicyclo[4.3.0]non-5-ene), antipyrine and dimethylphenylamine, can be used for this purpose. The reacting amine can be used neat, or as solution in water, or lower alkyl alcohol, such as methanol, ethanol, n-propanol and isopropanol and 1 to 2 molar equivalents is used. The conversion reaction is carried out at temperatures ranging from about $-30°$ to about $60°$ C.

As for the hydrogenation from the compound (IV) to the compound (V), an ethereal solvent such as THF, an alcoholic solvent, such as methanol, water, an aromatic solvent, such as toluene, benzene or xylene, an ester solvent, such as ethyl acetate or any compositional mixture thereof is used as a reaction medium. The hydrogenation from the compound (IV) to the compound (V) is carried out at a temperature of about −10° to about 150° C. under about 1 to about 100 atm hydrogen pressure. This reaction is performed in the presence of a catalyst, such as palladium, platinum, platinum oxide, rhodium, and iridium.

Concrete examples of the anhydrous acid used for the preparation of the compound (I) from the compound (V) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid and hydroxyethane sulfonic acid and the like. For additional acids, one can refer to "Pharmaceutical Salts", J. Pharm. Sci., 1977; 66 (1): 1–19. This preparation is executed in a reaction media which can be exemplified by an ethereal solvent such as THF, an alcoholic solvent such as methanol, an ester solvent such as ethyl acetate, an aromatic solvent, and any compositional mixture thereof. An ethereal solvent is recommended as an addition solution, including ethyl ether, propyl ether, isopropyl ether, butyl ether, isobutyl ether. The concentration of the compound (V) is on the order of about 0.01 to about 5.00 mole.

The second method for preparing the novel compounds of the general structural formula (V) are described in detail below.

O-Carbamoyl-phenylalaninols of structural formula (II) are reacted with Di-t-butyl dicarbonate to synthesize N-t-butyloxycarbonyl-phenylalaninol represented by the general formula (VII):

Then, the compound of structural formula (VII) is subjected to treatment with 1,1'-carbonyldiimidazole in an ethereal solution, a halogenated hydrocarbon solution or mixtures thereof, followed by treatment in the presence of an amine base, represented by the following general structural formula (VI):

wherein $R^1$ and $R^2$ are the same as defined above, to yield O-carbamoyl-N-t-butyloxycarbonyl-phenylalaninol represented by the general formula VIII:

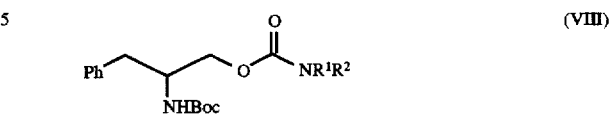

wherein Ph, $R^1$ and $R^2$ are as defined above. Then, this intermediate is deprotected by aqueous hydrochloric acid solution. As a result of the deprotection, there is obtained O-carbamoyl-phenylalaninol represented by the general formula (V). Without further purification, the compound of formula (V) may be converted into pharmaceutically acceptable salts (I) as described above.

This procedure for preparing the compound of structural formula (I) is summarized in Reaction Scheme II set forth below.

REACTION SCHEME II

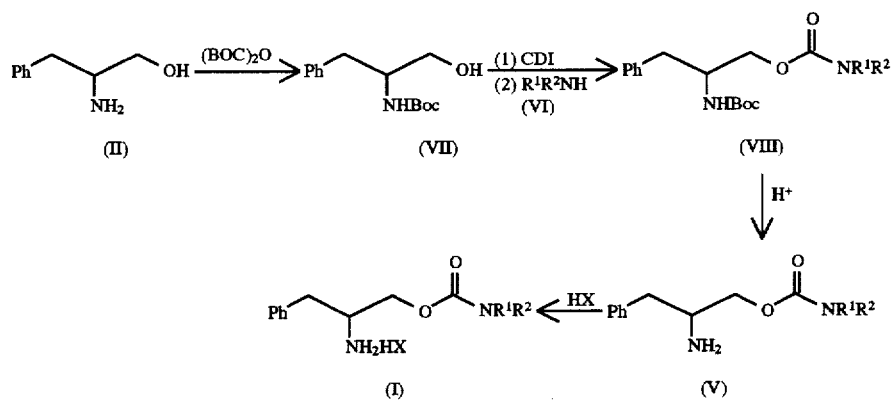

Details of the reaction conditions described in Reaction Scheme II are as follows. In the first step, the concentration of the starting material (VII) is about 0.005 to about 3 moles with 1,1'-carbonyldiimidazole ranging from about 1.0 to about 2.0 equivalents. This reaction is preferably carried out at a temperature of about −10° to about 70° C. Without purification, the resulting intermediate is treated with from about 1 to about 1,000 equivalents of ammonia at a temperature of about −30° to about 30° C., to give the compound of the general formula (VIII). For this carbamoylation, an ethereal solvent such as diethyl ether and tetrahydrofuran, a halogenated hydrocarbon solvent such as dichloromethane and chloroform, or mixtures thereof, may be used. The compound of general formula (VIII) (about 0.005 to about 3 moles) is treated with aqueous 1 to 12N hydrochloric acid at a temperature of about −10° to about 30° C., followed by neutralization.

In Reaction Scheme II, HX represents an acid capable of forming a pharmacologically useful salt with the basic nitrogen atom.

Representative examples of the compound (V and IX) from Reaction Scheme I and II are shown in Table I:

TABLE 1

Examples of the compound (V and IX) from Reaction Scheme I and II.

| $R_x$ | $R^1$ | $R^2$ | $R_x$ | $R^1$ | $R^2$ |
|---|---|---|---|---|---|
| H | H | Me | H | Me | Me |
| H | H | Et | H | Et | Et |
| H | H | n-Pr | H | H | i-Pr |
| H | H | c-Pr | H | H | n-Bu |
| H | H | c-Hex | H | H | n-Oct |
| H | H | Bn | H | H | $C_6H_5$ |
| H | H | o-F—$C_6H_4$ | H | H | o,p-$F_2$—$C_6H_3$ |
| H | — | (S)-2-Bu | H | — | pyrrolidinyl |
| H | — | piperidinyl | H | — | morpholinyl |
| H | — | 4-Ph-piperazinyl | H | — | 4-Me-piperazinyl |
| o-F— | H | H | p-Cl— | H | Me |
| m-F— | H | H | p-Cl— | H | i-Pr |
| p-F— | H | H | m-F— | H | Me |
| p-Cl— | H | H | m-F— | H | Et |
| p-NO2— | H | H | m-F— | H | iPr |
| p-MeS— | H | H | m-F— | Me | Me |
| p-HO— | H | H | p-MeO— | H | Me |
| p-MeO | — | pyrrolidinyl | o-MeO— | — | piperidinyl |
| 3,4-(HO)$_2$— | H | Ph | 3,4-(MeO)$_2$— | H | Me |
| 3,4-(MeO)$_2$— | H | H | 3,4-(MeO)$_2$— | Me | Me |
| 3,4-$Cl_2$— | H | H | 3,4-$Cl_2$— | H | iPr |

For therapeutic use in medicines for treating pain, depression, anxiety, epilepsy, stroke, dementual and Parkinson's disease, the compounds of the present invention, alone or in combination with a pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of the patient's condition and the activity of the compound. The determination of optimum dosages for a particular situation must be determined clinically and is within the skill of the art.

In utilizing the compounds of the present invention for the central nervous system, particularly to treat depression, it is preferred to administer the compounds orally. Since the compounds are well absorbed, when administered orally, it usually will not be necessary to resort to parenteral administration. For oral administration, the compound (I) is preferably combined with a pharmaceutical carrier. The ratio of the carrier to the compound of Structural Formula (I) is not critical to express the effects of the medicine on the central nervous system, and they can vary considerably depending on whether the composition is to be filled into capsules or formed into tablets. In tableting, various edible pharmaceutical carriers or the mixture thereof can be used. A suitable carrier, for example, is a mixture of lactose, diabasic calcium phosphate and/or corn starch. Other pharmaceutically acceptable ingredients can also be added, including lubricants such as magnesium stearate.

Besides the compound of structural formula (I), compositions comprising it are within the scope of the present invention. Furthermore, the present invention includes uses of the compound (I) and/or the composition.

A better understanding of the present invention may be obtained in light of following examples which are set forth to illustrate, but are not to be construed to limit, the present invention.

EXAMPLE 1

Preparation of O-Carbamoyl-N-(t-Butyloxycarbonyl)-o-Fluorophenylalaninol

In a 250 mL flask equipped with magnetic stirrer, N-(t-butyloxycarbonyl)-o-fluorophenylalaninol (0.096 mole, 2.15 g) was dissolved in 200 ml of THF and was added with 1,1'-carbonyldiimidazole (0.010 mol, 1.62 g) at 0° C. The reaction mixture was stirred at room temperature for 2 hours, followed by the injection of ammonia at 0° C. for 30 min. Following elevating to room temperature, water was added to terminate the reaction. The organic layer was extracted 3 times with dichloromethane, dried over magnesium sulfate and distilled in vacuo, to give a solid. This was recrystalized in a solution mixture of n-hexane and diethyl ether, to produce 1.93 g of O-carbamoyl-N-(t-butyloxycarbonyl)-o-fluorophenylalaninol: Yield 75%.

¹H-NMR (CDCl₃, 200 MHz), ppm (δ): 1.45 (s, 9H), 2.88 (d, 2H), 4.09 (s, 2H), 4.60–4.83 (br, 2H), 6.99–7.32 (m, 4H)

EXAMPLE 2

Preparation of O-Carbamoyl-N-(t-Butyloxycarbonyl)-p-Fluorophenylalaninol

The procedure given in Example 1 was followed using N-(t-butyloxycarbonyl)-p-fluorophenylalaninol as a starting material, instead of N-(t-butyloxycarbonyl)-o-fluorophenylalaninol, to give 2.91 g of the title compound. A yield of 88% was obtained.

¹H-NMR (CDCl₃, 200 MHz), ppm (δ): 1.45 (s, 9H), 2.68–2.95 (m, 2H), 4.02 (s, 2H), 4.60–4.90 (br, 2H), 6.85–7.29 (m, 4H)

EXAMPLE 3

Preparation of O-Carbamoyl-N-(t-Butyloxycarbonyl)-p-Nitrophenylalaninol

The procedure given in Example 1 was followed using N-(t-butyloxycarbonyl)-p-nitrophenylalaninol as a starting material, instead of N-(t-butyloxycarbonyl)-o-fluorophenylalaninol, to give 2.66 g of the title compound. A yield of 76% was obtained.

¹H-NMR (CDCl₃, 200 MHz), ppm (δ): 1.25 (s, 9H), 2.60–2.82 (m, 1H), 2.85–3.05 (m, 1H), 3.80–4.10 (m, 3H), 6.52 (s, 1H), 6.90 (d, 1H), 7.45 (d, 2H), 8.20 (d, 2H)

EXAMPLE 4

Preparation of O-Carbamoyl-N-(t-Butyloxycarbonyl)-p-(t-Butyloxycarbonyloxy)-Phenylalaninol The procedure given in Example 1 was followed using N-(t-butyloxycarbonyl)-p-(t-butyloxycarbonyloxy) phenylalaninol as a starting material, instead of N-(t-butyloxycarbonyl)-o-fluorophenylalaninol, to give 2.55 g of the title compound. A yield of 68% was obtained.

¹H-NMR (CDCl₃, 200 MHz), ppm (δ): 1.38 (s, 9H), 1.55 (s, 9H), 2.70–2.92 (m, 2H), 3.68–3.81 (m, 1H), 3.98–4.12 (m, 3H), 4.68–4.91 (br, 2H), 7.01–7.31 (m, 4H)

EXAMPLE 5

Preparation of O-Carbamoyl-N-Benzyloxycarbonyl-m-Fluorophenylalaninol

In a 100 mL flask equipped with magnetic stirrer, N-benzyloxycarbonyl-m-fluorophenylalaninol (0.007 mole, 2.12 g) was dissolved in 50 ml of THF and was added with 1,1'-carbonyldiimidazole (0.007 mol, 1.14 g) at 0° C. The reaction mixture was stirred at room temperature for 2 hours, followed by the injection of ammonia at 0° C. for 30 min. Following elevating to room temperature, water was added to terminate the reaction. The organic layer was extracted 3 times with dichloromethane, dried over magnesium sulfate and distilled in vacuo, to give a solid. This was recrystalized in a solution mixture of n-hexane and diethyl ether, to produce 2.18 g of O-carbamoyl-N-benzyloxycarbonyl-m-fluorophenylalaninol: Yield 91%.

¹H-NMR (CDCl₃, 200 MHz), ppm (δ): 2.49–2.98 (m, 2H), 3.69–4.15 (m, 4H), 4.80–5.12 (m, 2H), 6.35–6.75 (br, 2H), 6.80–7.60 (m, 9H)

EXAMPLE 6

Preparation of O-Carbamoyl-o-Fluorophenylalaninol Hydrochloride

In a 100 mL flask equipped with magnetic stirrer, O-carbamoyl-N-(t-butyloxycarbonyl)-o-fluorophenylalaninol obtained in Example 1 was dissolved in 40 ml of THF and was added with 20 ml of 6N aqueous hydrochloric acid solution. The reaction mixture was stirred at room temperature for 8 hours, followed by the neutralization with saturated aqueous potassium carbonate solution. Thereafter, the organic layer was extracted 3 times with dichloromethane, dried over magnesium sulfate and distilled in vacuo, to give a yellowish liquid. This was dissolved in 30 ml of THF and added with anhydrous hydrochloric acid at 0° C., to obtain desirable white precipitates. To this was added 30 ml of anhydrous ether, with the aim of maximizing the precipitation. As a result, 1.22 g of the title compound was obtained: Yield 73%.

Melting point: 160°–161° C.

¹H-NMR (DMSO-d₆, 200 MHz), ppm (δ) : 2.82–3.18 (m, 2H), 3.40–3.70 (br, 1H), 3.72–4.18 (m, 2H), 6.62 (s, 2H), 7.08–7.58 (m, 4H), 8.45 (br, 3H)

EXAMPLE 7

Preparation of O-Carbamoyl-p-Fluorophenylalaninol Hydrochloride

The procedure given in Example 6 was followed using O-carbamoyl-N-(t-butyloxycarbonyl)-p-fluorophenylalaninol as a starting material, to give the title compound.

Melting point: 111°–113° C.

¹H-NMR (DMSO-d₆, 200 MHz), ppm (δ) : 2.85–3.20 (m, 2H), 3.20–3.60 (br, 1H), 3.80–4.20 (m, 2H), 6.65 (s, 2H), 6.98–7.45 (m, 4H), 8.45 (br, 3H)

EXAMPLE 8

Preparation of O-Carbamoyl-p-Nitrophenylalaninol Hydrochloride

The procedure given in Example 6 was followed using O-carbamoyl-N-(t-butyloxycarbonyl)-p-nitrophenylalaninol obtained in Example 3 as a starting material, to yield the title compound.

¹NMR (DMSO-d₆, 200 MHz), ppm (δ) : 3.04(d—d, 1H), 3.22 (d—d, 2H), 3.67 (br, 1H), 3.94 (d—d, 1H), 4.06 (dd, 1H), 6.63 (s, 2H), 7.62 (d,2H), 8.24 (d, 2H), 8.53 (br, 3H)

EXAMPLE 9

Preparation of O-Carbamoyl-p-Hydroxy-Phenylalaninol Hydrochloride

The procedure given in Example 6 was followed using O-carbamoyl-N-(t-butyloxycarbonyl)-p-(t-butyloxycarbonyloxy) phenylalaninol obtained in Example 4 as a starting material, to yield the title compound.

Melting point: 213°–214° C.

¹H-NMR (DMSO-d6, 200 MHz), ppm (δ): 2.58–3.11 (m, 2H), 3.50–3.72 (br, 1H), 3.78–4.15 (m, 2H), 6.65 (s, 2H), 7.10 (d, 2H), 8.35 (br, 3H), 9.48 (s, 1H)

EXAMPLE 10

Preparation of O-Carbamoyl-m-Fluorophenylalaninol Hydrochloride

In a 500 mL Parr reactor, O-carbamoyl-N-benzyloxy carbonyl-m-fluoro phenylalaninol (0.006 mole, 2.18 g)

obtained in Example 5 was dissolved in 50 mL of anhydrous methanol and added with palladium (carbon powder 10%, 0.10 g) Then, the reactor was closed and purged with hydrogen. The reaction was completed in 7 hours under hydrogen pressure of 50 psi at room temperature, which was confirmed on thin layer chromatography. The catalyst was filtered off. Thereafter, the organic layer thus obtained was concentrated through distillation into 1.08 g (99 %) of pale yellow liquid. The liquid was poured in 30 mL of anhydrous THF and cooled to 0° C. Anhydrous hydrochloric acid was then added, to give a desirable white precipitate. Addition of 30 mL of anhydrous ether maximized the precipitation. Filtration provided 1.24 g of the title compound.

Melting point: 144°–145° C.

$^1$H-NMR (DMSO-d6, 200 MHz), ppm (δ): 2.85–3.15 (m, 2H), 3.50–3.72 (br, 1H), 3.82–4.15(m,2H), 6.65 (s, 2H), 7.08–7.28 (m, 3H), 7.30–7.51 (m, 1H), 8.38 (br, 3H)

EXAMPLE 11

Preparation of O-(N-Methyl)-Carbamoyl-N-Benzyloxycarbonyl-D-Phenylalaninol

In a 250 mL flask, N-benzyloxycarbonyl-D-phenylalaninol (3.14 g, 0.011 mol) was dissolved in 150 ml of anhydrous THF under a nitrogen atmosphere and was added with antipyrine (2.27 g, 0.012 mol). The reaction mixture was cooled to 0° C. in an ice/water bath and phosgene (6.05 mL of 2M solution in toluene, 0.012 mol) was added at one try. After stirring for 1 hour, methylamine (0.38 g, 0.012 mol) was added. Following stirring at ambient temperatures for an extra 4 hours, water was added to terminate the reaction. The organic layer was extracted 3 times with dichloromethane, dried over magnesium sulfate and distilled in vacuo, to give a solid. This was recrystalized in a solution mixture of ethyl acetate and diethyl ether, to produce 2.93 g of O-(N-methyl)-carbamoyl-N-benzyloxycarbonyl-D-phenylalaninol: Yield 78%.

$^1$H-NMR (CDCl$_3$, 200 MHz), ppm (δ): 2.58–2.98 (m, 5H), 3.98–4.22 (br, 3H), 4.58–4.75 (br, 1H), 5.08 (s, 3H), 7.12–7.48 (m, 10H)

EXAMPLE 12

Preparation of O-(N-Isopropyl)-Carbamoyl-N-Benzyloxycarbonyl-D-Phenylalaninol

The procedure given in Example 11 was followed using isopropyl amine as a reactant, instead of methyl amine, to give O-(N-isopropyl)-carbamoyl-N-benzyloxycarbonyl-D-phenylalaninol. A yield of 88% was obtained.

$^1$H-NMR (CDCl$_3$, 200 MHz), ppm (δ): 1.25 (d, 6H), 2.72–3.02 (m,2H), 3.68–3.90 (m, 1H), 3.98–4.25 (m, 3H), 4.51–4.65 (br, 1H), 5.18 (s, 3H), 7.08–7.51 (m,10H)

EXAMPLE 13

Preparation of O-(N-n-Octyl)-Carbamoyl-N-Benzyloxycarbonyl-D-Phenylalaninol

The procedure given in Example 11 was followed using n-octyl amine as a reactant, instead of methyl amine, to give O-(N-n-octyl)-carbamoyl-N-benzyloxycarbonyl-D-phenylalaninol. A yield of 96% was obtained.

$^1$H-NMR (CDCl$_3$, 200 MHz), ppm (δ) : 0.85 (t, 3H), 1.08–1.58 (m, 12H), 2.72–2.98 (m, 2H), 3.15 (q, 2H), 3.39–4.26 (m, 3H), 3.39–4.26 (m, 3H), 4.65–4.78 (br, 1H), 5.10 (s, 3H), 7.08–7.48 (m, 10H)

EXAMPLE 14

Preparation of O-(N-Cyclohexyl)-Carbamoyl-N-Benzyloxycarbonyl-D-Phenylalaninol

The procedure given in Example 11 was followed using cyclohexyl amine as a reactant, instead of methyl amine, to give O-(N-cyclohexyl)-carbamoyl-N-benzyloxycarbonyl-D-phenylalaninol. A yield of 79% was obtained.

$^1$H-NMR (CDCl$_3$, 200 MHz), ppm (δ) : 0.95–2.05 (m, 10H), 2.68–3.02 (m, 2H), 3.32–3.58 (m, 1H), 3.90–4.25 (br, 3H), 4.58–4.75 (m, 1H), 5.10 (s, 3H), 7.01–7.56 (m, 10H)

EXAMPLE 15

Preparation of O-(N,N-Dimethyl)-Carbamoyl-N-Benzyloxycarbonyl-D-Phenylalaninol

The procedure given in Example 11 was followed using dimethyl amine as a reactant, instead of methyl amine, to give O-(N,N-dimethyl)-carbamoyl-N-benzyloxycarbonyl-D-phenylalaninol. A yield of 94% was obtained.

$^1$H-NMR (CDCl$_3$, 200 MHz), ppm (δ): 2.55–3.05 (br, 6H), 3.85–4.28 (m, 3H), 4.90–5.48 (m, 4H), 6.80–7.70 (m, 10H)

EXAMPLE 16

Preparation of O-(N-Pyrrolidyl)-Carbamoyl-N-Benzyloxycarbonyl-D-Phenylalaninol

The procedure given in Example 11 was followed using pyrrolidine as a reactant, instead of methyl amine, to give O-(N-pyrrolidyl)-carbamoyl-N-benzyloxycarbonyl-D-phenylalaninol. A yield of 80% was obtained.

$^1$H-NMR (CDCl$_3$, 200 MHz), ppm (δ): 1.85–2.05 (br, 4H), 2.82–3.18 (m, 2H), 3.18–3.48 (m, 4H), 3.92–4.28 (m, 3H), 5.08 (s, 2H), 5.12–5.31 (m, 1H), 6.98–7.55 (m, 10H)

EXAMPLE 17

Preparation of O-(N-Piperidyl)-Carbamoyl-N-Benzyloxycarbonyl-D-Phenylalaninol

The procedure given in Example 11 was followed using piperidine as a reactant, instead of methyl amine, to give O-(N-piperidyl)-carbamoyl-N-benzyloxycarbonyl-D-phenylalaninol. A yield of 80% was obtained.

$^1$H-NMR (CDCl$_3$, 200 MHz), ppm (δ) : 1.35–1.85 (br, 6H), 2.72–3.05 (m, 2H), 3.32–3.58 (m, 4H), 3.95–4.38 (m, 3H), 5.05–5.28 (m, 3H), 7.05–7.52 (m, 10H)

EXAMPLE 18

Preparation of O-(N-Morpholino)-Carbamoyl-N-Benzyloxycarbonyl-D-Phenylalaninol

The procedure given in Example 11 was followed using morpholine as a reactant, instead of methyl amine, to give O-(N-morpholino)-carbamoyl-N-benzyloxycarbonyl-D-phenylalaninol. A yield of 85% was obtained.

$^1$H-NMR (CDCl$_3$, 200 MHz), ppm (δ): 2.72–3.02 (m, 2H), 3.25–3.55 (br, 4H), 3.55–3.80 (br, 4H), 3.95–4.30 (m, 3H), 5.15 (s, 3H), 7.05–7.51 (m, 10H)

EXAMPLE 19

Preparation of O-[N-(N-Phenyl)piperazino]-Carbamoyl-N-Benzyloxycarbonyl-D-Phenylalaninol The procedure given in Example 11 was followed using N-phenylpiperazine as a reactant, instead of methyl amine, to give O-[N-(N-phenyl)piperazino]-carbamoyl-N-benzyloxycarbonyl-D-phenylalaninol. A yield of 93% was obtained.

$^1$H-NMR (CDCl$_3$, 200 MHz), ppm ($\delta$): 2.72–3.02 (m, 2H), 3.05–3.23 (br, 4H), 3.45–3.75 (br, 4H), 4.02–4.31 (m, 3H), 5.10 (s, 3H), 6.80–7.50 (m, 15H)

EXAMPLE 20

Preparation of O-(N-Methyl)-Carbamoyl-D-Phenylalaninol Hydrochloride

In a 500 mL Parr reactor, O-(N-methyl)-carbonyl-N-benzyloxycarbonyl-D-phenylalaninol (2.80 g) obtained in Example 11 was dissolved in 80 mL of anhydrous methanol and palladium (carbon powder 10%, 0.10 g) was added. Then, the reactor was closed and purged with hydrogen for 1 min. The reaction was completed in 7 hours under 50 psi hydrogen pressure at ambient temperatures, which was confirmed on thin layer chromatography. The catalyst was filtered off. Thereafter, the organic layer thus obtained was concentrated through distillation into 1.43 g (84%) of pale yellow liquid. The liquid was poured in 30 mL of anhydrous THF and cooled to 0° C. Anhydrous hydrochloric acid was then added, to give a desirable white precipitate. Addition of 30 mL of anhydrous ether maximized the precipitation. Filtration provided 1.36 g of the title compound as a white solid: Yield 68%.

Melting point=162°–163° C.

$^1$H-NMR (DMSO-d$_6$, 200 MHz), ppm ($\delta$) 2.28–3.18 (m, 2H), 3.48–3.75 (br, 1H), 3.80–4.22 (m, 2H), 6.98–7.65 (m, 6H), 8.45 (br, 3H)

EXAMPLE 21

Preparation of O-(N-Isopropyl)-Carbamoyl-D-Phenylalaninol Hydrochloride

The title compound was prepared in a similar manner to that of Example 20, except that O-(N-isopropyl)-carbamoyl-N-benzyloxycarbonyl-D-phenylalaninol was used as the starting material.

Melting Point: 170°–171° C.

$^1$H-NMR (DMSO-d$_6$, 200 MHz), ppm ($\delta$) 1.08 (d, 6H), 2.82–3.18 (m, 2H), 3.48–3.75 (m, 2H), 3.85–4.15 (m, 2H), 7.15 (s, 1H), 7.22–7.45 (m, 5H), 8.45 (br, 3H)

EXAMPLE 22

Preparation of O-(N-Octyl)-Carbamoyl-D-Phenylalaninol Hydrochloride

The title compound was prepared in a similar manner to that of Example 20, except that O-(N-octyl)-carbamoyl-N-benzyloxycarbonyl-D-phenylalaninol was used as the starting material.

Melting Point: 105°–106° C.

$^1$H-NMR (DMSO$_6$, 200 MHz), ppm ($\delta$): 1.08 (t, 3H), 1.18–1.55 (m, 12H), 2.78–3.16 (m, 4H), 3.62 (br, 1H), 3.82–4.15 (m, 2H), 7.15 (t, 1H), 7.25–7.45 (m, 5H), 8.35 (br, 3H)

EXAMPLE 23

Preparation of O-(N-Cyclohexyl)-Carbamoyl-D-Phenylalaninol Hydrochloride

The title compound was prepared in a similar manner to that of Example 20, except that O-(N-cyclohexyl)-carbamoyl-N-benzyloxycarbonyl-D-phenylalaninol was used as the starting material.

Melting Point: 232°–233° C.

$^1$H-NMR (DMSO-d$_6$, 200 MHz), ppm ($\delta$) 0.98–1.88 (m, 10H), 2.78–3.16 (m, 2H), 3.25 (br, 1H), 3.65 (br, 1H), 3.82–4.12 (m, 2H), 7.15 (d, 1H), 7.22–7.45 (m, 5H), 8.35 (br, 1H)

EXAMPLE 24

Preparation of O-(N,N-Dimethyl)-Carbamoyl-D-Phenylalaninol Hydrochloride

The title compound was prepared in a similar manner to that of Example 20, except that O-(N,N-dimethyl)-carbamoyl-N-benzyloxycarbonyl-D-phenylalaninol was used as the starting material.

Melting Point: 129°–130° C.

$^1$H-NMR (DMSO-d$_6$, 200 MHz), ppm ($\delta$) 2.65–2.99 (m, 6H), 2.99–4.16 (m, 5H), 7.05–7.45 (m, 5H), 8.48 (br, 3H)

EXAMPLE 25

Preparation of O-(N-Pyrrolidyl)-Carbamoyl-D-Phenylalaninol Hydrochloride

The title compound was prepared in a similar manner to that of Example 20, except that O-(N-pyrrolidyl)-carbamoyl-N-benzyloxycarbonyl-D-phenylalaninol was used as the starting material.

Melting Point: 224°–225° C.

$^1$H-NMR (DMSO$_6$, 200 MHz), ppm ($\delta$) 1.52–1.98 (m, 4H), 2.72–3.76 (m, 7H), 3.78–4.22 (m, 2H), 7.02–7.52 (m, 5H), 8.58 (br, 3H)

EXAMPLE 26

Preparation of O-(N-Piperidyl)-Carbamoyl-D-Phenylalaninol Hydrochloride

The title compound was prepared in a similar manner to that of Example 20, except that O-(N-piperidyl)-carbamoyl-N-benzyloxycarbonyl-D-phenylalaninol was used as the starting material.

Melting Point: 190°–191° C.

$^1$H NMR (DMSO$_6$, 200 MHz), ppm ($\delta$): 1.18–1.72 (m, 6H), 2.68–3.76 (m, 7H), 3.78–4.22 (m, 2H), 7.02–7.52 (m, 5H), 8.58 (br, 3H)

EXAMPLE 27

Preparation of O-(N-Morpholino)-Carbamoyl-D-Phenylalaninol Hydrochloride

The title compound was prepared in a similar manner to that of Example 20, except that O-(N-morpholino)-carbamoyl-N-benzyloxycarbonyl-D-phenylalaninol was used as the starting material.

Melting Point: 207°–208° C.

$^1$H-NMR (DMSO-d$_6$, 200 MHz), ppm ($\delta$) : 2.76–3.25 (m, 2H), 3.25–3.82 (m, 9H), 3.86–4.22 (m, 2H), 7.12–7.52 (m, 5H), 8.48 (br, 3H)

EXAMPLE 28

Preparation of O-[N-(N-Phenyl)piperazino]-Carbamoyl-D-Phenylalaninol Hydrochloride The title compound was prepared in a similar manner to that of Example 20, except that O-[N-(N-phenyl)piperazino]

carbamoyl-N-benzyloxycarbonyl-D-penylalaninol was used as the starting material.

Melting Point: 241°–242° C.

$^1$H-NMR (CDCl$_3$, 200 MHz), ppm (δ): 2.76–4.32 (m, 13H), 6.98–7.82 (m, 10H), 8.72 (br, 3H)

EXAMPLE 29

Preparation of O-Carbamoyl-p-hydroxy-(D)-phenylalaninol Hydrochloride

The procedure given in Example 6 was followed using O-carbamoyl-N-(t-butyloxycarbonyl)-p-(t-butyloxycarbonyloxy)-(D)-phenylalaninol as the starting material, to yield the title compound.

Melting point=223°–224° C.

$^1$H-NMR(DMSO-d$_6$, 200 MHz), ppm (δ): 2.62–3.05(m, 2H), 3.35–3.65(br., 1H), 3.72–4.15(m,2H), 6.55(s,2H), 6.65 (d,2H), 7.08 (d,2H), 8.32 (br.,3H), 9.45 (s, 1H).

EXAMPLE 30

O-(N-Isopropyl)-Carbamoyl-D-Phenylalaninol Hydrochloride

The title compound was prepared and it possess following properties.

Melting Point: 153°–154° C.

$^1$H-NMR (DMSO-d$_6$, 300 MHz), ppm (δ) 0.87 (t, 3H), 1.44 (m, 2H), 2.86–3.02 (m, 3H), 3.14 (d—d, 1H), 3.57 (m, 1H), 3.99 (d—d, 1H), 4.09 (d—d, 1H), 6.83 (br, 1H), 7.24–7.36 (m, 5H), 8.46 (br, 3H)

EXAMPLE 31

O-(N-(S)-Butyl)-Carbamoyl-D-Phenylalaninol Hydrochloride

The title compound was prepared and it possess following properties.

Melting point=190°–191° C.

$^1$H-NMR (DMSO-d$_6$, 200 MHz), ppm (δ) : 0.82 (t, 3H), 1.08 (d, 3H), 1.42 (m, 2H), 2.82–3.18 (m, 2H), 3.49–3.79 (m, 2H), 3.85–4.18 (m, 2H), 7.01 (d, 1H), 7.18–7.55 (m, 5H), 8.42 (br, 3H).

EXAMPLE 32

O-[N-(N-Methyl)piperazino]-Carbamoyl-D-Phenylalaninol Hydrochloride

The title compound was prepared and it possess following properties.

Melting point=130°–131° C.

$^1$H-NMR (DMSO-d6, 200MHz), ppm (δ) : 2.75 (s, 3H), 2.85–3.69 (m., 11H), 3.85–4.32 (m, 2H), 7.09–7.55 (m, 5H), 8.65 (br, 3H).

EXAMPLE 33

O-(N-Benzyl)-Carbamoyl-D-Phenylalaninol Hydrochloride

The title compound was prepared and it possess following properties.

Melting Point: 159°–162° C.

$^1$H-NMR (DMSO-d$_6$, 300 MHz), ppm (δ) 2.79–3.05 (m, 2H), 3.57 (br, 1H), 3.87–4.08 (m, 2H), 4.18 (d, 2H), 7.20–7.35 (m, 10H), 7.70 (t, 1H), 8.35 (br, 3H).

EXAMPLE 34

O-(N-Phenyl)-Carbamoyl-D-Phenylalaninol Hydrochloride

The title compound was prepared and it possess following properties.

Melting Point: 200°–201° C.

$^1$H-NMR (DMSO-d$_6$, 200 MHz), ppm (δ) 2.81–3.18 (m, 2H), 3.77–3.85 (m, 1H), 4.08 (d—d, 1H), 4.28 (d—d, 1H), 7.02–7.68 (m, 10H), 8.32 (br, 3H), 9.75 (s, 1H).

EXAMPLE 35

O-(N-o-Fluorophenyl)-Carbamoyl-D-Phenylalaninol Hydrochloride

The title compound was prepared and it possess following properties.

Melting Point: 190°–191° C.

$^1$H-NMR (DMSO-d$_6$, 200 MHz), ppm (δ) 2.92 (d—d, 1H), 3.12 (d—d, 1H), 3.55–3.75 (m, 1H), 4.02 (d—d, 1H), 4.19 (d—d, 1H), 6.98–7.55 (m, 8H), 7.75 (t, 1H), 8.58 (br, 3H), 9.35 (s, 1H).

EXAMPLE 36

O-(N-o,p-Difluorophenyl)-Carbamoyl-D-Phenylalaninol Hydrochloride

The title compound was prepared and it possess following properties.

Melting Point: 189°–190° C.

$^1$H-NMR (DMSO-d$_6$, 200 MHz), ppm (δ) 2.92 (d—d, 1H), 3.12 (d—d, 1H), 3.55–3.75 (m, 1H), 4.02 (d—d, 1H), 4.19 (d—d, 1H), 6.98–7.55 (m, 8H), 7.75 (t, 1H), 8.58 (br, 3H), 9.35 (s, 1H).

EXAMPLE 37

O-Carbamoyl-3-Chlorophenylalaninol Hydrochloride

The title compound was prepared and it possess following properties.

Melting Point: 176°–176.3° C.

$^1$H-NMR (DMSO-d$_6$, 200 MHz), ppm (δ) : 2.72–3.18 (m, 2H), 3.48–3.62 (br, 1H), 3.82–4.15 (m, 2H), 6.55 (s, 2H), 7.08–7.65 (m, 4H), 8.49 (br, 3H).

EXAMPLE 38

O-Carbamoyl-D-3,4-Dichlorophenylalaninol Hydrochloride

The title compound was prepared and it possess following properties.

$^1$H-NMR (DMSO-d$_6$, 300 MHz), ppm (δ): 2.87–3.08 (m, 2H), 3.57 (m, 1H), 3.92–4.08 (m, 2H), 6.43 (br, 2H), 7.28–7.37 (m, 1H), 7.50–7.59 (m, 2H), 8.37 (br, 3H).

EXAMPLE 39

O-Carbamoyl-3,4-Dihydroxyphenylalaninol Hydrochloride

The title compound was prepared and it possess following properties.

Melting Point: 205°–206° C.

¹H-NMR (DMSO-d₆, 200 MHz), ppm (δ) : 2.55–2.95 (m, 2H), 3.32–3.69 (br, 1H), 3.79–4.18 (m, 2H), 6.38–6.96 (m, 5H), 8.25 (br, 3H), 8.99 (br, 2H).

EXAMPLE 40

O-(N-Isopropyl)-Carbamoyl-D-4-ChloroPhenylalaninol Hydrochloride

The title compound was prepared and it possess following properties.

Melting Point: 173°–175° C.

¹H-NMR (DMSO-d₆, 300 MHz), ppm (δ) 2.87–3.12 (m, 2H), 3.51–3.65 (m, 2H), 3.96–4.11 (m, 2H), 6.56 (br, 1H), 7.29–7.37 (m, 4H), 8.33 (br, 3H).

As described hereinbefore, the compounds represented by Structural Formula I were observed to be useful for the prophylaxis and treatment of CNS disorders including pain, depression, anxiety, epilepsy, stroke, demential and Parkinson's disease.

The present invention has been described in an illustrative manner, and it is to be understood that the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A racemic or enantiomerically enriched O-carbamoyl-phenylalaninol compound represented by the following structural formula V:

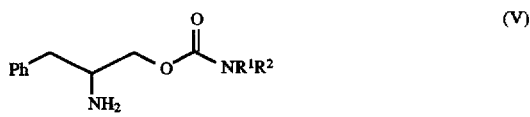

(V)

wherein Ph is a phenyl group as described as follows:

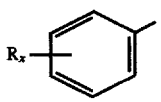

wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms, and x is an integer from 1 to 3, with the proviso that R is the same or different when x is 2 or 3, R¹ and R² are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and R¹ and R² are joined to form a 5 to 7-membered cyclic compound optionally containing zero to one additional nitrogen atom substituted with a member selected from the group consisting of hydrogen, alkyl, and aryl groups, or zero to one oxygen atom directly unconnected, excluding the instance where R, R¹, and R² are all hydrogen, and the pharmaceutically acceptable salts thereof.

2. The O-carbamoyl-phenylalaninol compound represented by the structural formula V, in accordance with claim 1, wherein R is hydrogen, and pharmaceutically acceptable salts thereof.

3. The O-carbamoyl-phenylalaninol compound represented by the structural formula V, in accordance with claim 1, wherein R is hydrogen, R¹ and R² may be the same or different from each other and are independently selected from the group consisting of hydrogen, lower alkyl of 1 to 8 carbon atoms, aryl, arylalkyl, cyclic propyl and 5 to 7-membered aliphatic cyclic compounds, with the proviso when R¹ and R² are same, it is not hydrogen, and the pharmaceutically acceptable salts thereof.

4. The O-carbamoyl-phenylalaninol compound represented by the structural formula V, in accordance with claim 1, wherein R is hydrogen, R¹ and R² may be joined to form a 5 to 7-membered cyclic compound which may comprise zero to one additional nitrogen atom substituted with a member selected from the group consisting of hydrogen, alkyl, and aryl groups, or zero to one oxygen atom directly unconnected, and the pharmaceutically acceptable salts thereof.

5. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, and pharmaceutically acceptable salts thereof.

6. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, and pharmaceutically acceptable salts thereof.

7. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, and pharmaceutically acceptable salts thereof.

8. The O-carbamoyl-phenylalaninol compound represented by the structural formula V, in accordance with claim 1, wherein R¹ and R² are hydrogen, R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, and pharmaceutically acceptable salts thereof.

9. The O-carbamoyl-phenylalaninol compound represented by the structural formula V, in accordance with claim 1, wherein R¹ and R² are hydrogen, R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, and pharmaceutically acceptable salts thereof.

10. The O-carbamoyl-phenylalaninol compound represented by the structural formula V, in accordance with claim 1, wherein R¹ and R² are hydrogen, R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, and pharmaceutically acceptable salts thereof.

11. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and the pharmaceutically acceptable salts thereof.

12. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and the pharmaceutically acceptable salts thereof.

13. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and the pharmaceutically acceptable salts thereof.

14. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, $R^1$ and $R^2$ are joined to form a 5 to 7-membered cyclic compound optionally containing zero to one additional nitrogen atom substituted with a member selected from the group consisting of hydrogen, alkyl, and aryl groups, or zero to one oxygen atom directly unconnected, and the pharmaceutically acceptable salts thereof.

15. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, $R^1$ and $R^2$ are joined to form a 5 to 7-membered cyclic compound optionally containing zero to one additional nitrogen atom substituted with a member selected from the group consisting of hydrogen, alkyl, and aryl groups, or zero to one oxygen atom directly unconnected, and the pharmaceutically acceptable salts thereof.

16. The O-carbamoyl-phenylalaninol compound represented by the structural formula V, in accordance with claim 1, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, $R^1$ and $R^2$ are joined to form a 5 to 7-membered cyclic compound optionally containing zero to one additional nitrogen atom substituted with a member selected from the group consisting of hydrogen, alkyl, and aryl groups, or zero to one oxygen atom directly unconnected, and the pharmaceutically acceptable salts thereof.

17. The O-carbamoyl-phenylalaninol compound represented by the structural formula V, in accordance with claim 1, which is selected from the group consisting of the following structural formulas:

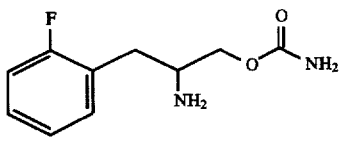

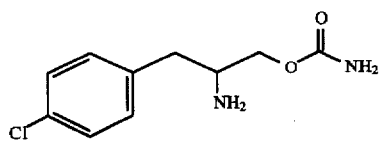

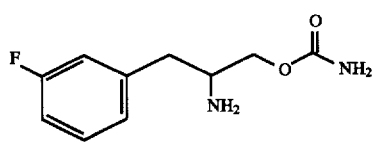

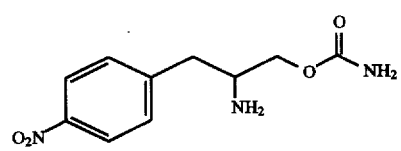

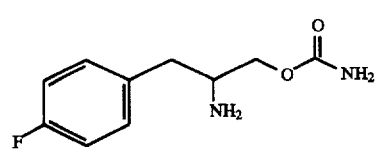

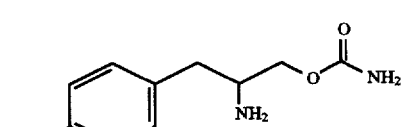

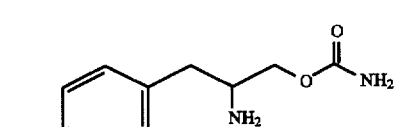

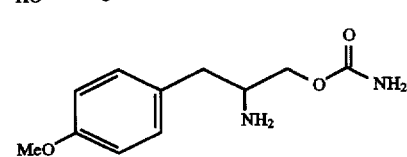

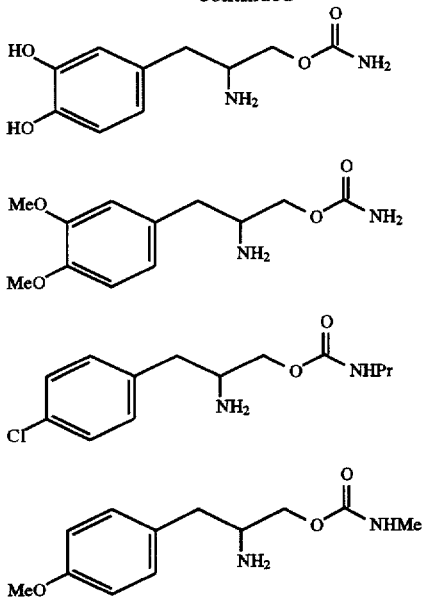

and pharmaceutically acceptable salts thereof.

18. An enantiomerically enriched O-carbamoyl-(D)-phenylalaninol compound represented by the structural formula IX:

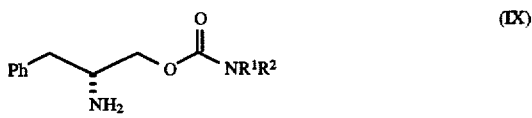

wherein Ph is a phenyl group as described as follows:

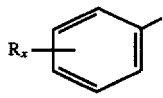

wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms, and x is an integer from 1 to 3, with the proviso that R is the same or different when x is 2 or 3, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and $R^1$ and $R^2$ are joined to form a 5 to 7-membered cyclic compound which may comprise zero to one additional nitrogen atom substituted with a member selected from the group consisting of hydrogen, alkyl, and aryl groups, or zero to one oxygen atom directly unconnected, excluding the instance where R, $R^1$, and $R^2$ are all hydrogen, and the pharmaceutically acceptable salts thereof.

19. The O-carbamoyl-(D)-phenylalaninol compound represented by the structural formula IX, in accordance with claim 18, wherein R is hydrogen, and pharmaceutically acceptable salts thereof.

20. The O-carbamoyl-(D)-phenylalaninol compound represented by the structural formula IX, in accordance with claim 18, wherein R is hydrogen, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, with the proviso when $R^1$ and $R^2$ are same, it is not hydrogen, and the pharmaceutically acceptable salts thereof.

21. The O-carbamoyl-(D)-phenylalaninol compound represented by the structural formula IX, in accordance with claim 18, wherein R is hydrogen, $R^1$ and $R^2$ are joined to form a 5 to 7-membered cyclic compound optionally containing zero to one additional nitrogen atom substituted with a member selected from the group consisting of hydrogen, alkyl, and aryl groups, or zero to one oxygen atom directly unconnected, and the pharmaceutically acceptable salts thereof.

22. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, and pharmaceutically acceptable salts thereof.

23. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, and pharmaceutically acceptable salts thereof.

24. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, and pharmaceutically acceptable salts thereof.

25. The O-carbamoyl-(D)-phenylalaninol compound represented by the structural formula IX, in accordance with claim 18, wherein $R^1$ and $R^2$ are hydrogen, R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, and pharmaceutically acceptable salts thereof.

26. The O-carbamoyl-(D)-phenylalaninol compound represented by the structural formula IX, in accordance with claim 18, wherein $R^1$ and $R^2$ are hydrogen, R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, and pharmaceutically acceptable salts thereof.

27. The O-carbamoyl-(D)-phenylalaninol compound represented by the structural formula IX, in accordance with claim 18, wherein $R^1$ and $R^2$ are hydrogen, R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, and pharmaceutically acceptable salts thereof.

28. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and the pharmaceutically acceptable salts thereof.

29. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and the pharmaceutically acceptable salts thereof.

30. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, $R^1$ and $R^2$ are the same or different from each other and are independently selected from the group consisting of hydrogen, lower alkyl of 1 to 8 carbon atoms, aryl, arylalkyl, cyclic propyl and 5 to 7-membered aliphatic cyclic compounds, and the pharmaceutically acceptable salts thereof.

31. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is an integer from 1 to 3, with the proviso that R is the same or different when x is 2 or 3, $R^1$ and $R^2$ are joined to form a 5 to 7-membered cyclic compound which may comprise zero to one additional nitrogen atom substituted with a member selected from the group consisting of hydrogen, alkyl, and aryl groups, or zero to one oxygen atom directly unconnected, and the pharmaceutically acceptable salts thereof.

32. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms and hydroxy, x is an integer from 1 to 3, with the proviso that R is the same or different when x is 2 or 3, $R^1$ and $R^2$ are joined to form a 5 to 7-membered cyclic compound optionally containing zero to one additional nitrogen atom substituted with a member selected from the group consisting of hydrogen, alkyl, and aryl groups, or zero to one oxygen atom directly unconnected, and the pharmaceutically acceptable salts thereof.

33. The O-carbamoyl-(D)-phenylalaninol compound represented by the structural formula IX, in accordance with claim 18, wherein R is a member selected from the group consisting of lower alkyl of 1 to 8 carbon atoms, halogen selected from F, Cl, Br and I, alkoxy containing 1 to 3 carbon atoms, nitro, hydroxy, trifluoromethyl, or thioalkoxy containing 1 to 3 carbon atoms, x is 1, $R^1$ and $R^2$ are joined to form a 5 to 7-membered cyclic compound optionally containing zero to one additional nitrogen atom substituted with a member selected from the group consisting of hydrogen, alkyl, and aryl groups, or zero to one oxygen atom directly unconnected, and the pharmaceutically acceptable salts thereof.

34. An enantiomerically enriched O-carbamoyl-(D)-phenylalaninol compound represented by the structural formula IX:

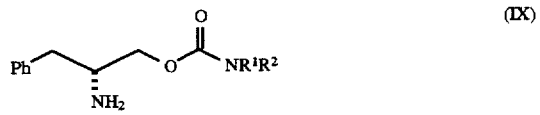

(IX)

wherein Ph is a phenyl group as described as follows:

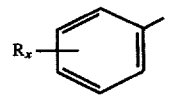

wherein $R^1$ and $R^2$ may be the same or different from each other and are independently selected from the group consisting of hydrogen, lower alkyl of 1 to 8 carbon atoms, 5 to 7-membered aliphatic cyclic compounds, with the proviso when $R^1$ and $R^2$ are same, it is not hydrogen, and the pharmaceutically acceptable salts thereof.

35. The O-carbamoyl-phenylalaninol compound represented by the structural formula IX, in accordance with claim 18, which is selected from the group consisting of the following structural formulas:

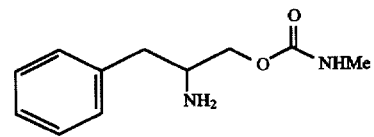

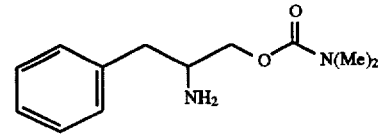

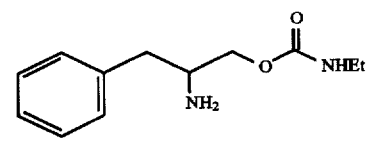

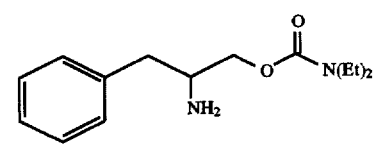

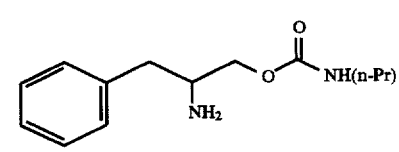

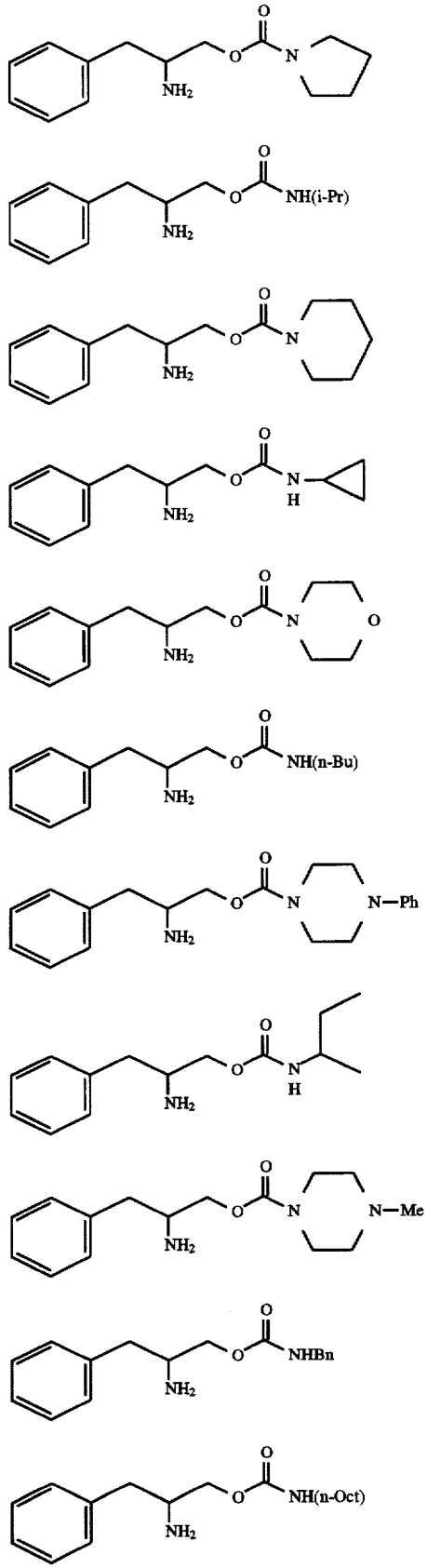
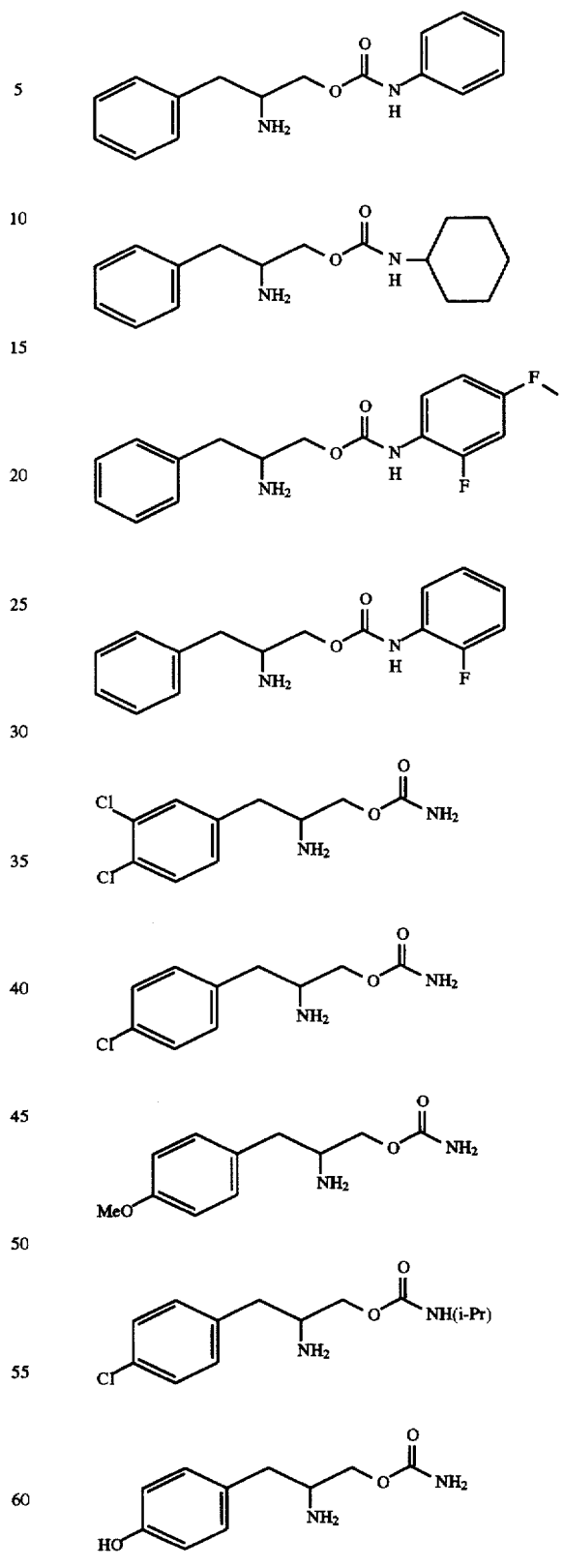

27
-continued
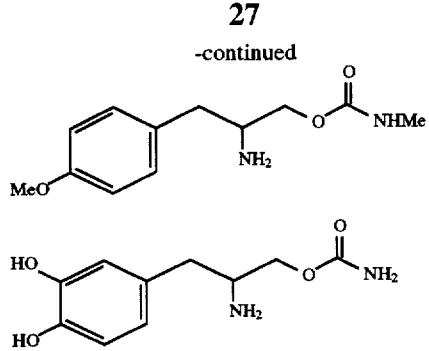
28
-continued
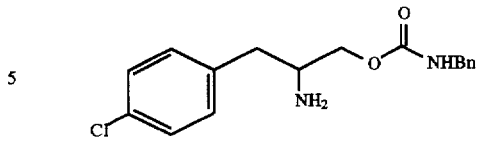
and pharmaceutically acceptable salts thereof.
* * * * *

(12) REEXAMINATION CERTIFICATE (4312nd)
United States Patent
Choi et al.

(10) Number: US 5,756,817 C1
(45) Certificate Issued: Apr. 17, 2001

(54) O-CARBAMOYL-PHENYLALANINOL COMPOUNDS, THEIR PHARMACEUTICALLY USEFUL SALTS AND PROCESS FOR PREPARING THE SAME

(75) Inventors: Yong Moon Choi, Towaco, NJ (US); Dong Il Han, Taejon (KR); Yong Kil Kim, Taejon (KR); Hun Woo Shin, Taejon (KR); Jeong-Han Park, Flanders, NJ (US)

(73) Assignee: SK Corporation, Fairfield, NJ (US)

Reexamination Request:
No. 90/005,501, Sep. 22, 1999

Reexamination Certificate for:
Patent No.: 5,756,817
Issued: May 26, 1998
Appl. No.: 08/726,675
Filed: Oct. 7, 1996

Related U.S. Application Data

(63) Continuation-in-part of application No. 08/596,496, filed on Feb. 5, 1996, now Pat. No. 5,705,640.

(30) Foreign Application Priority Data

Feb. 11, 1995 (KR) .................................... 1995-2543

(51) Int. Cl.[7] .................................... C07C 261/00
(52) U.S. Cl. .................. 560/115; 544/172; 544/389; 546/226; 548/531; 560/32; 560/163; 560/164
(58) Field of Search .................. 560/115, 32, 163, 560/164; 544/172, 389; 546/226; 548/531

(56) References Cited

FOREIGN PATENT DOCUMENTS 14334826    5/1976  (GB) .

*Primary Examiner*—Michael L. Shippen

(57) ABSTRACT

The present invention relates to a racemic or enantiomerically enriched O-carbamoyl-phenylalaninol compound represented by the following structural formula V and pharmaceutically acceptable salts thereof to treat diseases of the central nervous system:

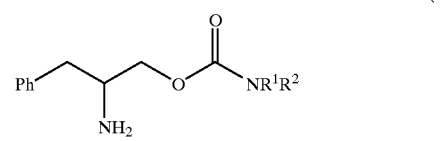

wherein Ph is a phenyl group as described as follows:

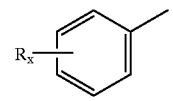

wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms, and x is an integer from 1 to 3, with the proviso that R is the same or different when x is 2 or 3. $R^1$ and $R^2$ may be the same or different from each other and are independently selected from the group consisting of hydrogen, lower alkyl of 1 to 8 carbon atoms, aryl, arylalkyl, cyclic propyl and 5 to 7-membered aliphatic cyclic compounds, and $R^1$ and $R^2$ may be joined to form a 5 to 7-membered cyclic compound which may comprise zero to one additional nitrogen atom substituted with a member selected from the group consisting of hydrogen, alkyl, and aryl groups, or zero to one oxygen atom directly unconnected, excluding the instance where R, $R^1$, and $R^2$ are all hydrogen, and the pharmaceutically acceptable salts thereof.

The present invention also relates to O-carbamoyl-(D)-phenylalaninol compounds, represented by the following structural formula IX:

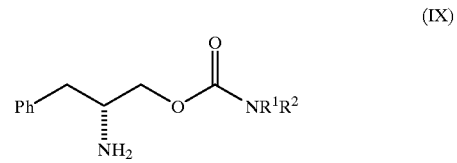

wherein Ph, $R^1$, and $R^2$ are as described above, and the pharmaceutically acceptable salts thereof.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–35 is confirmed.

* * * * *